United States Patent [19]

Fritig et al.

[11] Patent Number: 5,959,178
[45] Date of Patent: Sep. 28, 1999

[54] MODIFICATION OF LIGNIN SYNTHESIS IN PLANTS

[75] Inventors: Bernard Jean Meinrad Fritig, Souffelweyersheim, France; Jan Van Doorsselaere, Gent; Dirk Gustaaf Inzé, Aalst, both of Belgium; Lise Jouanin, Versailles Cedex, France; Mary Elizabeth Knight, Heathlake Park Crowthorne, United Kingdom; Marc van Montagu, Gent, Belgium; Michel Legrand, Pfettisheim, France

[73] Assignee: Imperial Chemical Industries PLC, United Kingdom

[21] Appl. No.: 08/204,288

[22] PCT Filed: Sep. 9, 1992

[86] PCT No.: PCT/GB92/01640

§ 371 Date: Oct. 27, 1994

§ 102(e) Date: Oct. 27, 1994

[87] PCT Pub. No.: WO93/05160

PCT Pub. Date: Mar. 18, 1993

[30] Foreign Application Priority Data

Oct. 9, 1991 [GB] United Kingdom ............... 9119270

[51] Int. Cl.$^6$ .............. A01H 5/00; C12N 15/82
[52] U.S. Cl. ............. 800/298; 435/419; 435/320.1; 536/23.6
[58] Field of Search .................. 800/205, 250, 800/298; 536/23.6; 435/69.1, 172.3, 240.4, 320.1, 419

[56] References Cited

FOREIGN PATENT DOCUMENTS 2005597  6/1990  Canada .

OTHER PUBLICATIONS

Gowri et al: "Stress responses in Alflfa (Medicago *Sativa* L.)", *Plant Physiology*, vol. 97, No. 1, Sep. 1991, pp. 7–14, see the whole document, particularly p. 13, right col. last para.

Campbell et al: "Seasonal expression of a lignin specific O–methyltransferase cloned from aspen developing secondary xylem", *J.Cell.Biochem.Suppl.*, Meeting Held Jan. 10–17, 1991, vol. 15a, 1991, p. 144, see whole document.

Jaeck et al: "Regulation of enzymes involved in lignin biosynthesis: Induction of O–methyltransferase mRNAs during the hypersensitive reaction of tobacco to tobacco mosaic virus", Biological Abstracts, vol. 94, 1992, Abstract No. 89217, & *Mol Plant–Microbe Interact*, vol. 5, No.4, 1992, pp. 294–300.

Ni et al: "Modification of lignin biosynthesis by genetic manipulaton of caffeic acid O–methyltransferase" *J.Cell-.Biochem.Suppl.*, Meeting Held Apr. 10–16, 1992, vol. 16F, 1992, p. 219, see abstract Y219.

Podila et al: "Antisense expression of an aspen O–methyltransferase construct in transgenic tobacco via Agrobacterium", *Plant Physiology*, vol. 99, No. 1, May 1992, p. 19, see abstract 110.

Lagrimini et al: "Wound–induced deposition of polyphenols in transgenic plants overexpressing peroxidase", *Plant Physiology*, vol. 96, No.2, Jun. 1991, pp. 577–583, see the whole document.

Bugos et al: "Cloning and Expression of Lignin Bispecific O–Methyl Transferase", *Plant Physiology*,vol.93, No.1, May 1990, p. 15.

Biological Abstracts, vol. 84 (1987), See abstract No 19249.

Biological Abstracts, vol. 73 (1982), See abstract No 64323.

Dumas et al (Jul. 12, 1991) Sequence Database Accession No. M73431, Locus POPOME.

Napoli et al (1990) The Plant Cell 2: 279–289.

van der Kol et al (1988) Nature 333: 866–869.

Finnegan et al (1994) Bio/Technology 12: 883–887.

Lewin (1987) Science 237: 1570.

*Primary Examiner*—Elizabeth F. McElwain
*Attorney, Agent, or Firm*—Cushman Darby & Cushman; IP Group of Pillsbury; Madison & Sutro LLP

[57] ABSTRACT

The biosynthesis of lignin in plants is regulated by insertion into the plant genome by altering the plant's ability to synthesise the enzyme O-methyl transferase, an enzyme involved in the lignin biosynthetic pathway. Production of O-methyl-transferase may be enhanced by insertion into the plant genome by transformation of one or more additional copies of the O-methyl-transferase gene or production may be inhibited by insertion of a gene encoding anti-sense mRNA directed against the mRNA encoded by the endogenous O-methyl-transferase gene.

9 Claims, 10 Drawing Sheets

Fig. 1

```
   1 CACCTTCTTCAACCTTTTGTTCCTTAAAGAATTCAATCTTGATCAAGATGGGTTCAACAGTGAAACTCAGAGACTCAACTCAGTATCA        15
                                                 M  G  S  T  G  E  T  Q  M  T  P  T  Q  V  S
  94 GATGAAGAGGCACACCTCTTTGCCATGCAACTAGCCAGTGCTTCAGTTCTACCAAACAGCCATTGAACTCGACCTTCTTGAA             46
      D  E  E  A  H  L  F  A  M  Q  L  A  S  A  S  V  L  P  M  I  L  K  T  A  I  E  L  D  L  L  E
 187 ATCATGGCTAAAGCTGGCCCTGGTGCTTTCTTGTCCACATCTGAGATAGCTTCTCACCTCCCTACCAAAAACCCTGATGCGCCTGTCATGTTA  77
      I  M  A  K  A  G  P  G  A  F  L  S  T  S  E  I  A  S  H  L  P  T  K  N  P  D  A  P  V  M  L
 280 GACCGTATCTTGCGCCTCCTGGCTAGCTACTCCATATCTTGAAAGATCATCCTGAAAGTTGAGAGACTGTATGGCCTT                 108
      D  R  I  L  R  L  L  A  S  Y  S  I  L  I  C  S  L  K  D  H  P  D  G  K  V  E  R  L  Y  G  L
 373 GCTCCTGTTTGCAAATTCTTGACCAAGAACGAGGACGGTGTCTCTCCATTAACAAGGCCTATGGGGATGACTGCATTTGAATATCATGGACGGATCCA  139
      A  P  V  C  K  F  L  T  K  N  E  D  G  V  S  V  S  P  L  C  L  M  N  P  D  K  V  L  M  E  S
 466 TGGTATTATTTGAAAGATGCAATTCTTGATGGAGAATTCCATTTAACAAGGCCTATGGGGATGACTGCATTTGAATATCATGGAACGGATCCA   170
      W  Y  Y  L  K  D  A  I  L  D  G  G  I  P  F  N  K  A  Y  G  M  T  A  F  E  Y  H  G  T  D  P
 559 AGATTCAACAAGGTCTTCAATAAGGGAATGTCTGACCACTCTGAGCTGTCGTTAACACCATCGTCTCTAAATACCCTTCAATTAAGGCATTAACTTTGATTTG  201
      R  F  N  K  V  F  N  K  G  M  S  D  H  S  T  I  T  M  K  K  I  L  E  T  Y  K  G  F  E  G  L
 652 ACATCCTTGGTGGATGTTGGTGGGACTGGAGCTGTGTTATCCGGTGAGCAGCATGTTGTTAGTGTGCCAAAGCAGATGCCGTTTC          232
      T  S  L  V  D  V  G  G  T  G  A  V  V  N  T  I  V  S  K  Y  P  S  I  K  G  I  N  F  D  L
 745 CCCCACGTCATTGAGGATGCCATGCCCATCTTATCCGGTGAGCAGCATGTTGGTGGAGAATTGCTATGACGCCTTGCCGGAAAACGGCAAGGTGATA       263
      P  H  V  I  E  D  A  P  S  Y  P  G  V  E  H  V  G  G  D  M  F  V  S  V  P  K  A  D  A  V  F
 838 ATGAAGTGGATATGCCATGACTGGAGCGACGCCACACTGCTTAAAATTCTTGAAGAATTCTTGAAGACGCCCTTGCCGGAAAACGGCAAGTATGGCAAGGTGATA  294
      M  K  W  I  C  H  D  W  S  D  A  H  C  L  K  F  L  K  N  C  Y  D  A  L  P  E  N  G  K  Y  I
 931 CTTGTTGAGTGCATTCTTCCCGTGGCTCCTGACACAAGCCTTGCCACCAAGGGAGTCGTTCACATTGATGTTATCATGCTGGCGCCACAACCCC         325
      L  V  E  C  I  L  P  V  A  P  D  T  S  L  A  T  K  G  V  V  H  I  D  V  I  M  L  A  H  N  P
1028 GGTGGGAAAGACAGAGAGACTGAGAAAGGACCGAAAAGGAACTAAGGGAGCTTAGCTAAGGAGCTGGCTGCTGCATGTGCATTCAACACA            356
      G  G  K  E  R  T  E  K  E  F  E  G  L  A  K  G  A  G  F  Q  G  F  E  V  M  C  C  A  F  N  T
1121 CATGTCATTGAGTTACTGGGGTTTCCAAGCTCCAAGTTACTGGGGTTTCCATACAACGTTGCTGTCTCTGCTTTTG                   364
      H  V  I  E  L  R  K  N
1214 ATGTTGTGATTGCTTTTTACATGACGAGTAGCTTTCTCTTATGAAAACATGTAAGGTTGCGTTTGTATGCCTGATTTCTCAAATA
1307 ACTTCACTGCCTCCCCTCCAAATTCTTAATACATGTGAAAGATTCTTAAAAAAAAAAAAAAAAA
```

Fig. 2A

```
  1  GCCGGCCCGG GCGCGGGCGAT TTCTCCTTCT GAATTAGCTG CTCAGCTCTC
 51  AACCCAGAAC CCAGAAGCAC CCGTTATGCT TGATCGGATG CTTAGGCTAC
101  TTGCTACTTA CTCTGTTCTC AATTGTACTC TTAGAACACT GTCTGATGGC
151  AGTGTTGAGA GGCTTTATAG TCTGGCTCCG GTTTGTAAGT TCTTGACTAA
201  GAATGCTGAT GGTGTTTGTG TTGCCCCACT TTTGCTTATG AATCAAGATA
251  AAGTTCTTAT GGAGAGCTGG TACCACTTAA AAGATGCAGT ACTAGATGGT
301  GGAATCCCAT TCAACAAGGC CTATGGAATG ACAGCATTTG AGTACCATGG
351  CACAGATCCA AGATTCAACA AAGTTTTCAA CCGTGGAATG TCTGATCACT
401  CCACTATGTC AATGAAAAAG ATTCTTGAGG ACTACAAAGG ATTTGAAGGC
451  CTAAATTCCA TTGTCGATGT TGGTGGTGGA ACTGGGCGCTA CTGTTAACAT
501  GATTGTCTCC AAACATCCCT CTATTAAGGG TATTAACTTT GATTTACCAC
551  ATGTTATTGG AGATGCTCCA GCTTACCCTG GTGTCGAGCA CGTTGGTGGC
601  GACATGTTTG CCAGTGTGCC AAAAGCAGAT GCCATTTTCA TGAAGTGGAT
```

```
651   TTGTCATGAT TGGAGCGACG AGCATTGCCT AAAATTCTTG AAGAATTGCT
701   ATGAAGCACT ACCTGCAAAT GGGAAGGTGA TAATAGCGGA GTGCATACTT
751   CCAGAGGCCC CAGATACATC ACTTGCAACT AAGAATACAG TACATGTTGA
801   TATTGTGATG TTAGCACATA ACCCAGGAGG CAAAGAAAGG ACTGAGAAGG
851   AATTTGAGGC TTTGGCTAAG GGCGCTGGTT TTACTGGATT CGCAAGGCTT
901   GTTGCGCTTA CAACACTTGG GTCATGGAAT TCAACAAATA ATTAATCGAT
951   TCCTTTGGAG AATTAAGCAA TATACTGTTC ATTTTGCATT TTGAAATTCT
1001  ACTTTTCACA GAGTGGCTTT ACTGCGAAAT AAAAGAAATA TATAGCTTTT
1051  ACCTTGAAAA GATCAATGTT CAAAGGGAAA AAAAAAAGGA AGATGAAATA
1101  ATTGCTCTCA GAAAAGCAGT GTGTTAGGAA AAAGCTTTTT AGCTGGATTT
1151  TGAATTTTTA TTGTATGTAT TTCTGTAATA CACATGTATT GAAGGAATAC
1201  TAGTTTTCGA CCAATCATAT TTCTTTGAAA AAAAAAAAAA AAAA
```

```
ATTCCTTCAACTTACCCAATTAAGTCATCGAAAAATCTGAAACAGAACTAAAAGTAAAAT
1
                                                              M
TTATTTGCCATGCAATTGTGTAGTGCTTCTGTACTTCCTATGGTCCTAAAATCAGCCGTAGA
119
 L   F   A   M   Q   L   C   S   A   S   V   L   P   M   V   L   K   S   A   V   E
21
GAATTAGCTGCTCAGCTCTCAACTCAGAACCCAGAAGCACCTGTTATGCTTGATCGGATGCT
239
 E   L   A   A   Q   L   S   T   Q   N   P   E   A   P   V   M   L   D   R   M   L
61
AGTGTTGAGAGGCTTTATAGTCTGGCTCCCGTCTGTAAGTACTTGACTAAGAATGCTGATGG
359
 S   V   E   R   L   Y   S   L   A   P   V   C   K   Y   L   T   K   N   A   D   G
101
TACCACTTAAAAGATGCAGTACTAGATGGCGGAATCCCATTCAACAAAGCCTATGGAATGCA
419
 Y   H   L   K   D   A   V   L   D   G   G   I   P   F   N   K   A   Y   G   M
141
TCTGATCACTCCACTATGTCAATGAAGAAGATTCTTGAGGACTACAAAGGATTTGAAGGCCT
599
 S   D   H   S   T   M   S   M   K   K   I   L   E   D   Y   K   G   F   E   G   L
181
AAATATCCCTCTATTAAGGGCATTAACTTTGATTTGCCACATGTAATTGGAGATGCTCCAAC
719
 K   Y   P   S   I   K   G   I   N   F   D   L   P   H   V   I   G   D   A   P   T
221
GCCATTTTCATGAAGTGGATTTGTCATGATTGGAGCGATGAGCATTGCCTAAAATTCTTGAA
839
 A   I   F   M   K   W   I   C   H   D   W   S   D   E   H   C   L   K   F   L   K
261
CCAGAGGCCCCAGATACATCACTTGCAACTAAGAATACAGTACATGTTGATATTGTTATGTT
959
 P   E   A   P   D   T   S   L   A   T   K   N   T   V   H   V   D   I   V   M   L
301
GGCGCTGGTTTTACTGGATTCGCAAGGCTTGTTGCGCTTACAACACTTGGGTCATGGAATTC
179
 G   A   G   F   T   G   F   A   R   L   V   A   L   T   T   L   G   S   W   N   S
341
CATTTGGAAATTCTACTTTTCTCAGAGTGGCTTGACTGTGAAATAAAAGAAATATAGCTTTT
1199
AAAGCAATGTGTTAGGAAAAGCTTTTTTAGCTGGATTTTGAATTTTACTGTATGTATTTCT
1319
```

From Fig. 3A

Fig. 3B

```
GGGTTCAACAAGCGAGAGCCAGAGTAACAGTCTCACTCACACAGAAGACGAAGCTTTC
                                                        118
  G   S   T   S   E   S   Q   S   N   S   L   T   H   T   E   D   E   A   F
                                                         20
ACTTGACCTTCTTGAGCTAATGGCTAAGGCTGGTCCAGGTGCAGCTATTTCTCCTTCT
                                                        238
  L   D   L   L   E   L   M   A   K   A   G   P   G   A   A   I   S   P   S
                                                         60
TAGGCTACTTGCTTCTTACTCTGTTCTCAATTGTACTCTTAGAACACTGCCTGATAGC
                                                        358
  R   L   A   S   Y   S   V   L   N   C   T   L   R   T   L   P   D   S
                                                        100
TGTTTCTGTTGCCCCACTTTTGCTTATGAATCAAGATAAAGTTCTTATGGAGAGCTGG
                                                        418
  V   S   V   A   P   L   L   L   M   N   Q   D   K   V   L   M   E   S   W
                                                        140
AGCATTTGAGTACCATGGCACAGATCCAAGATTCAACAAAGTGTTCAACCGTGGAATG
                                                        598
  A   F   E   Y   H   G   T   D   P   R   F   N   K   V   F   N   R   G   M
                                                        180
AAATTCCATTGTTGATGTTGGTGGTGGAACGGGTGCTACTGTTAACATGATTGTCTCT
                                                        718
  N   S   I   V   D   V   G   G   G   T   G   A   T   V   N   M   I   V   S
                                                        220
TTACCCCGGTGTCGAGCACGTTGGTGGCGACATGTTTGCTAGTGTGCCAAAAGCAGAT
                                                        838
  Y   P   G   V   E   H   V   G   G   D   M   F   A   S   V   P   K   A   D
                                                        260
GAATTGCTATGAAGCACTACCTGCAAATGGGAAGGTGATAATTGCAGAGTGCATACTT
                                                        958
  N   C   Y   E   A   L   P   A   N   G   K   V   I   I   A   E   C   I   L
                                                        300
AGCACATAACCCAGGAGGCAAAGAAAGGACTGAGAAGGAATTTGAGGCTTTGGCTAAG
                                                       1078
  A   H   N   P   G   G   K   E   R   T   E   K   E   F   E   A   L   A   K
                                                        340
AACAAGTAATTAATCGATTCCTTAATTTGAAGGATTAAGCAATATACTGTTCGTTTTG
                                                       1198
  T   S   N   *
                                                        364
AACTTGAAAAGATTGATGTTCAAAAGAAAAAAGGAAGATGAAATAATTGCTCTCAGA
                                                       1318
GTTATACACATGTATTGAAGGAATACTAGTTTTCGACCAAAAAAAAAAAA
                                                       1431
```

Fig. 4A

```
  1   AACAAAAACACTCTAAAAGGAAAAGACTAGGAGAATAATTACACTACAACTCTTATAGCT

61   AATTCCTTGTCTCAAGATTTTCACCTATGGAATCCTCAACCAAAAGCCAAATACCAACACA
                            M  E  S  S  T  K  S  Q  I  P  T  Q   12

121   ATCAGAAGAAGAGCGTAACTGCACATATGCCAACTATTGTCATCTTCAGTCCTCCC
       S  E  E  E  R  N  C  T  Y  A  M  Q  L  L  S  S  V  L  P    32

181   CTTTGTGTTGCATTCAACAATTCAATTGGAAGTTTTTGAGATATTAGCCAAAATCTAATGA
       F  V  L  H  S  T  I  Q  L  E  V  F  E  I  L  A  K  S  N  D  52

241   CACTAAACTTTCTGCTTCTCAAATTGTTTCTCAAATTCCTAACTGCAAGAATCCTGATGC
       T  K  L  S  A  S  Q  I  V  S  Q  I  P  N  C  K  N  P  D  A  72
```

```
301  AGCTACTATGTTAGATAGGATGCTTTATGTTGTTGGCTAGTTACTCGTTGTTGTTTACTTGTTC
      A   T   M   L   D   R   M   L   Y   V   L   A   S   Y   S   L   F   T   C   S    92

361  CATTGTTGAGGATGAAGAAAAATAATGGGGGCCAGAAAAGAGTGTATGGTTTGTCACAAGT
      I   V   E   D   E   E   N   N   G   G   Q   K   R   V   Y   G   L   S   Q   V   112

421  GGGAAAATTCTTTGTTAGAGATGAAGATGGTGCATCAATGGGGCCACTTTTGGCTTTGCT
      G   K   F   F   V   R   D   E   D   G   A   S   M   G   P   L   L   A   L   L   132

481  TCAAGATAAAGTATTCATAAACAGCTGGTTTGAACTAAAAGATGCAGTTCTTGAAGGAGG
      Q   D   K   V   F   I   N   S   W   F   E   L   K   D   A   V   L   E   G   G   152

541  AGTTCCATTTGACAGGGTACACGGGTGTTGTCCATGCATTTGAATATCCAAAAATCGGACCC
      V   P   F   D   R   V   H   G   V   V   H   A   F   E   Y   P   K   S   D   P   172
```

From Fig. 4A

```
601 AAAATTCAATGATGTTTTCAACAAGGCAATGATCAATCACACAACTGTAGTCATGAAAAA
     K  F  N  D  V  F  N  K  A  M  I  N  H  T  T  V  V  M  K  K   192

661 AATACTTGAAAATTACAAAGGTTTTGAGAACCTTAAAACTTTGGTTGATGTTGGAGGTGG
     I  L  E  N  Y  K  G  F  E  N  L  K  T  L  V  D  V  G  G  G   212

721 TCTTGGAGTTAACCTCAAGATGATTACATCTAAATACCCCACAATTAAGGGCACTAATTT
     L  G  V  N  L  K  M  I  T  S  K  Y  P  T  I  K  G  T  N  F   232

781 TGATTTGCCACATGTTGTTCAACATGCCCCCTTCCTATCCTGGGGTGGAACATGTTGGGGG
     D  L  P  H  V  V  Q  H  A  P  S  Y  P  G  V  E  H  V  G  G   252

841 AGATATGTTTGAAAGTGTTCCAGAAGGAGATGCTATTTTTATGAAGTGGATTCTTCATGA
     D  M  F  S  V  P  E  G  D  A  I  F  M  K  W  I  L  H  D   272
```

From Fig. 4B

```
 901  CTGGAGTGATAGTCACAACCCTCAAGTTGCTAAAGAACTGCTACAAGGCTCTACCAGACAA
        W  S  D  S  H  N  L  K  L  L  K  N  C  Y  K  A  L  P  D  N   292

961  TGGAAAGGTGATTGTTGTTGAGGCCATTTTACCAGTGAAACCAGACATTGACACCGCAGT
        G  K  V  I  V  V  E  A  I  L  P  V  K  P  D  I  D  T  A  V   312

1021  GGTTGGCGTTTCGCAATGTGATTGATCATGATGGCTCAAAATCCTGGAGGCAAAGAGCG
        V  G  V  S  Q  C  D  L  I  M  M  A  Q  N  P  G  G  K  E  R   332

1080  ATCGGAAGAGGAGTTTCGAGCCTTGGCTACTGAAGCTGGATTCAAAGGCGTTAACTTAAT
        S  E  E  E  F  R  A  L  A  T  E  A  G  F  K  G  V  N  L  I   352

1141  ATGTTGTGTCTGTAATTTTTGGGTCATGGAATTCTGCAAGTAGATTTCTACTGTACATTG
```

From Fig. 4D

Fig. 4E

```
         C   C   V   C   F   P   W   V   M   E   F   C   K   *
1201  AGTTTCTACTACTCTTGAGTATCCATTTATGGCAATCTGGGACTGGAATTGCAGCTTAGT
1261  CCAGATTGAACATTGATATTCCTAATAATATTTCTATTATTTCCCTTGTTTATTTCTCTT
1321  GTATGAAAGGATGTCATTTGAGTATTGATAATCATGTTCTCTAGGACAGAAATTGTAAC
1381  TTTGTCCAACTTTATTGATATTCCTAGTAAGATTTATATGACATGTGTCTCTGGTTTGAG
1441  AAGAGTTTCAATATCTAAAAAAAAAAAAAAAAA
```

MODIFICATION OF LIGNIN SYNTHESIS IN PLANTS

BACKGROUND OF THE INVENTION

1. Field of the Invention

This invention relates to the improvement of plants by the modification of lignin biosynthesis, particularly, but not exclusively, the improvement of digestibility of fodder crops.

2. Background Information

Grassland farmers, and farmers of other fodder crops, face a difficult decision each year about when to cut their crops for conservation. All grass varieties of agricultural importance suffer from the disadvantage that during the normal increase in dry matter yield with growth, the digestibility decreases. The farmer, therefore, has, to compromise between a lower yield of highly digestible material and a higher yield of less digestible material. Another limitation is that harvesting at optimum maturity may be prevented by unfavourable weather. If the decline in digestibility could be controlled or delayed, higher yields of highly digestible material could be obtained and the prevailing weather conditions would not play such a major role in determining the quality of the harvested crop.

Digestibility of fodder crops is determined, among other factors, by the amount and quality of lignin deposition which has taken place during growth of the plants and the degree of secondary modification of lignin deposited. Beside cellulose and other poly-saccharides, lignins are an essential component of cell wall in tissues like the sclerenchyma and the xylem of vascular plants. They play an important role in the conducting function of the xylem by reducing the permeability of the cell wall to water. They are also responsible for the rigidity of the cell wall, and, in woody tissues, they act as a bonding agent between cells, imparting to the plant a resistance towards impact, compression and bending. Finally, they are involved in mechanisms of resistance to pathogens by impeding the penetration or the propagation of the pathogenic agent.

Lignins are not only important in the productivity and performance of field crops but are also of great importance in trees for paper making. Considerable energy and chemical input is required to loosen, dissolve and remove lignin from the cellulose fibre which is required for paper making. In addition to these instances in which lignins present a constraint on the use of crop plants, lignins are also used as feedstocks for the preparation of speciality chemicals such as phenolics which can be used as precursors in chemical synthesis. Thus lignins and their biological and chemical modification are important.

SUMMARY OF THE INVENTION

It is one of the objects of the present invention to provide a biotechnological procedure for the modification both lignin content and lignin composition in plants.

Lignins are the product of a dehydrogenative polymerisation of three primary precursors: the trans-coniferyl, trans-sinapyl and trans-p-coumaryl alcohols. The monomers can occur in lignins in different proportions and with different types of links both with each other and with the surrounding cell wall polysaccharides, thus producing a wide variety of polymers. These polymers, or "lignin cores" are always associated covalently with hemicelluloses. Most lignins also contain varying amounts of aromatic carboxylic acids in ester-like combinations. Such differences in the structure of lignins are usually found in plant species. However, differences in the composition of lignins, and even in the binding to the primary and secondary cell walls, can also occur in the same plant, between different tissues of different ages. The biosynthesis of lignin monomers (monolignols) is a part of the phenylpropanoid biosynthesis pathway, which is also responsible for the production of a wide range of compounds including flavonoid pigments, isoflavonoids, coumarin phytoalexins and cell division promoting dehydrodiconiferyl glucosides.

Phenylalanine is deaminated to produce cinnamic acid. This acid is then transformed by hydroxylation and methylation reactions, thus producing different acids substituted on the aromatic ring. The enzyme catalysing the methylation steps is O-methyl transferase (OMT). O-methyltransferases (S-adenosyl-L-methionine: O-methyltransferases; EC 2.1.1.6) thus play an important role in the biosynthesis of monolignols. By the O-methylation of caffeic acid and 5-hydroxyferulic acid, OMTs introduce one and two methoxy groups in the lignin monomers, respectively. The resulting two phenolics, ferulic acid and sinapic acid, respectively, are the precursors of coniferyl alcohol and sinapyl alcohol which are together with coumaryl alcohol substrates for peroxidases (Lewis and Yamamoto, 1990).

The previous methylation reactions are also used in the synthesis of several other phenolic compounds. However, in those cells which are dedicated to the production of lignins such as vascular xylem cells of plants, the OMT plays a crucial role in the production of the phenolic precursors incorporated into the lignin polymer. The cinnamyl alcohols, synthesised in the cytoplasm, are then transported to the cell wall where they are polymerised by peroxidase in the presence of hydrogen peroxide.

When the surface growth of the cell ceases, it is followed by a phase of wall thickening (secondary wall formation). Lignification takes place during this phase. It starts in the cell corners and extends along the middle lamella, through the primary wall and, finally, to the secondary wall. External factors can induce qualitative and quantitative modifications in lignification. The synthesis of new types of lignins, sometimes in tissues which are not normally lignified, may be induced by infection with pathogenic microorganisms. Lignification is stimulated by light, as well as by low calcium levels, by boron, by mechanical stress and by infection.

As a first step in unravelling of lignin biosynthesis at the molecular level, we have undertaken the biochemical characteristics and cloning of O-methyltransferases (OMTs). Previously three different OMTs (OMT I, OMT II, and OMT III) have been purified from tobacco. OMT I used mainly caffeic acid and 5-hydroxyferulic acid as a substrate and is the OMT actively present in healthy plants. OMT II and OMT III have a broader substrate specificity and also use catechol as substrate. Upon infection with TMV, an increase in activity of all three OMTs was shown. Based on this observation, it has been postulated that the OMT I is specifically involved in lignification, whereas OMT II and OMT III have a function in generating a lignin barrier upon infection. The importance of methylation in monolignol biosynthesis is well illustrated in brown-rib corn mutants. These plants exhibit a reduced lignin content and accumulate 5-hydroxyferulic acid) due to a low O-methyltransferase activity. Thus OMTs could be potential targets for modulation of lignification through the use of recombinant DNA technology.

Thus, plants with a reduced amount of lignin would be more efficiently used as a forage for cattle. The yield of milk and meat would be therefore increased. Furthermore, lignin may have a negative effect on plant growth. Thus, a reduction of the lignification in crops such as wheat, oilseed rape, sugar beet or maize might presumably increase the grain yield. Trees with reduced lignin contents or altered lignin structure will lead to a reduction in the cost of the paper as less lignin will have to be removed during the pulping process. On the other hand, novel papers may be produced due to the purity of cellulose fibre which could otherwise not be produced.

Reduction of lignification can be achieved by the application of chemical inhibitors to plants. However, a more effective method controlling lignin deposition and structure is the inhibition of expression of the CAD gene using antisense RNA. Antisense RNA technology is an appropriate molecular biology approach to the inhibition of lignification. An antisense RNA is an RNA produced by the transcription of the non-coding DNA strand (nonsense). Thus, antisense RNA has the same sequence as the coding DNA strand and is complementary to the mRNA product of a specific gene.

As is well known, a cell manufactures protein by transcribing the DNA of the gene for that protein to produce RNA, which is then processed (e.g. by the removal of introns) into messenger RNA and finally translated by ribosomes into protein. This process may be inhibited by the presence in the cell of "antisense RNA". Therefore, as used herein, the term "antisense RNA" means an RNA sequence which is complementary to a sequence of bases in a mRNA: complementary in the sense that each base (or a majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, preventing the formation of protein. How this works is uncertain: the complex may interfere with further transcription, processing, transport or translation, or lead to degradation of the mRNA, or have more than one of these effects. Such antisense RNA may be produced in the cell by transformation with an appropriate DNA construct arranged to transcribe backwards part of the coding strand (as opposed to the template strand) of the relevant gene (or of a DNA sequence showing substantial homology therewith).

The use of this technology to down-regulate the expression of specific plant genes has been described, for example in European Patent Publication No 271988 to ICI. Reduction of gene expression has led to a change in the phenotype of the plant: either at the level of gross visible phenotypic difference e.g. lack of lycopene synthesis in the fruit of tomato leading to the production of yellow rather than red fruit or at a more subtle biochemical level e.g. change in the amount of polygalacturonase and reduction in depolymerisation of pectins during tomato fruit ripening (Smith et al, Nature, 334, 724–726, 1988; Smith et al, Plant Mol Biol 14, 369–380, 1990). Thus antisense RNA has been proven to be useful in achieving down-regulation of gene expression in plants.

An object of the present invention is to provide plants having an altered ability to synthesise lignin.

According to the present invention there is provided the DNA insert contained in the clones pPLC4 and pTOMTI and variants thereof such as are permitted by the degeneracy of the genetic code or the functional equivalents thereof.

In addition, the present invention provides a recombinant DNA construct containing the said DNA under control of a transcriptional control sequence operative in plants, so that the construct can generate mRNA in plant cells.

For the down-regulation of lignin synthesis the aforesaid DNA is in antisense orientation.

For the amplification of lignin biosynthesis the aforesaid DNA is in sense orientation thus to provide one or more additional copies of the said DNA in the plant genome.

Thus, in a further aspect, the present invention provides DNA constructs comprising a transcriptional initiation region operative in plants positioned for transcription of a DNA sequence encoding RNA complementary to a substantial run of bases showing substantial homology to an mRNA encoding the protein produced by the gene in pPLC4 pTOMT1.

The invention further provides plant cells, and plants derived therefrom having stably incorporated in their genomes the aforesaid DNA in sense or antisense orientation, and fruit and seeds of such plants. The present invention is principally concerned with the suppression of lignin formation and, that being so, the inserted gene will be in antisense orientation, but there are instances where overproduction of lignin may have an advantageous effect, for example to improve plant stalk strength and resistance to diseases, and the present invention provides means for achieving amplification of the lignin biosynthetic ability of plants.

Thus the invention relates generally to the regulation of the plant's lignin biosynthetic pathway, in which OMT plays a dominant role, in order that the production of OMT, and hence the production and composition of lignin is altered by insertion of the OMT gene, or a portion thereof (usually of 50 or more bases), in antisense orientation so that the amount of OMT for catalysing lignin synthesis is reduced.

The constructs of the invention may be inserted into plants to regulate the production of the CAD enzyme. Depending on the nature of the construct, the production of the protein may be increased, or reduced, either throughout or at particular stages in the life of the plant. It is also possible to target the expression of the gene to a specific cell types of the plant, such as the epidermis, the xylem, the roots etc.

The plants to which the present invention can be applied include commercially important food and forage plants, such as alfalfa, maize, oil seed rape, forage grasses and sunflower, and but also tree crops such as eucalyptus, pine species and poplar.

DNA constructs according to the invention preferably comprise a sequence of at least 50 bases which is homologous to the DNA of the insert in pPLC4 or pTOMT1.A and pTOMT1.B. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

The preferred source of antisense RNA for use in the present invention is DNA derived from the clone pPLC4 or pTOMT1.A and pTOMT1.B. The required DNA encoding antisense RNA can be obtained in several ways: by cutting an appropriate sequence of DNA from pPLC4 or pTOMT1.A or pTOMT1.B (or any other source of the OMT gene); by synthesising a DNA fragment using synthetic oligonucleotides which are annealed and then ligated together in such a way as to give suitable restriction sites at each end; by using synthetic oligonucleotides in a polymerase chain reaction (PCR) to generate the required fragment with suitable restriction sites at each end. The DNA is then cloned into a vector containing upstream promoter and downstream terminator sequences, the cloning being carried out so that the DNA sequence is inverted with respect to its orientation to the promoter in the strand from which it was cut. In the new vector, the strand that was formerly the template strand becomes the coding strand, and vice versa. The new vector will thus encode RNA in a base sequence which is complementary to the sequence of pPLC4 and pTOMT1 mRNAs. Thus the two RNA strands are complementary not only in their base sequence but also in their orientations (5' to 3').

As source of the DNA base sequence for transcription, it is convenient to use a cDNA clone such as pPLC4. The base sequence of pPLC4 is shown in FIG. 1 (SEQ ID NO:1) and the base sequences of pTOMT1.A and pTOMT1.B is shown in FIG. 2 (SEQ ID NO:2).

The clone pPLC4 has been deposited at the National Collections of Industrial and Marine Bacteria, PO Box 31, of 23 St Machar Drive, Aberdeen AB2 1RY, Scotland, as a plasmid in E. coli, strain 'sure', under the reference NCIB 40436 on Aug. 22, 1991.

The clone pTOMT1.A has been deposited at the National Collections of Industrial and Marine Bacteria, PO Box 31, of 23 St Machar Drive, Aberdeen AB2 IRY, Scotland, as a plasmid in E. coli, strain DH5α, under the reference NCIB 40439 on Sep. 4, 1991.

The clone pTOMT1.B has been deposited at the National Collections of Industrial and Marine Bacteria, PO Box 31, of 23 St Machar Drive, Aberdeen AB2 1RY, Scotland, as a plasmid in E. coli, strain DH5α, under the reference NCIB 40440 on Sep. 4, 1991.

A source of DNA for the base sequence for transcription is the promoter of the OMT gene itself or other genes involved in lignification such as the promoter of the phenyl alanine ammonia lyase gene or its modified version which permits expression in xylem tissue, or the s-Adenosyl methionine synthase gene or the promoter of the extensin gene. Such a gene may differ from the cDNA of pPLC4 and pTOMT1.A or pTOMT1.B in that introns may be present. The introns are not transcribed into mRNA (or, if so transcribed, are subsequently cut out). When using such a gene as the source of the base sequence for transcription it is possible to use either intron or exon regions.

A further way of obtaining a suitable DNA base sequence for transcription is to synthesise it ab initio from the appropriate bases, for example using FIG. 1 and FIG. 2 as a guide. Recombinant DNA and vectors according to the present invention may be made as follows. A suitable vector containing the desired base sequence for transcription (for example pPLC4 and pTOMT1.A and pTOMT1.B) is treated with restriction enzymes to out cut the sequence. The DNA strand so obtained is cloned (in reverse orientation) into a second vector containing the desired promoter sequence (for example cauliflower mosaic virus 35S RNA promoter or the bean PAL promoter, Bevan et al, EMBO J.8, 1899–1906 1988) and the desired terminator sequence (for example the 3' of the Agrobacterium tumefaciens nopaline synthase gene.

In this invention we may use both constitutive promoters (such as cauliflower mosaic virus 35S RNA) and inducible or developmentally regulated promoters (such as the PAL gene promoter) as circumstances require. Use of a constitutive promoter will tend to affect functions in all parts of the plant: while by using a tissue specific promoter, functions may be controlled more selectively. The use of a tissue-specific promoter, has the advantage that the antisense or sense RNA is only produced in the tissue in which its action is required.

Vectors according to the invention may be used to transform plants as desired, to make plants according to the invention. Dicotyledonous plants, such as alfalfa, oil seed rape etc, may be transformed by Agrobacterium Ti plasmid technology, for example as described by Bevan (1984) Nucleic Acid Research, 12, 8711–8721. Such transformed plants may be replicated sexually, or by cell or tissue culture.

Poplar and aspen transformation using Agrobacterium tumefaciens can be performed as described by De Block [Plant Physiol. (1990) 93:1110–1116]. Stem internode pieces are used as a tissue source for incubation with an Agrobacterium tumefaciens strain (C58CRif$^R$(pMP90.)) harbouring chimeric marker genes (bar/neo) on its non-oncogenic T-DNA. For the aspen clone (Populus alba x P. tremula; clone 357, Afocel) and the poplar clone (Populus trichocarpa x P. deltoides; clone 064, Afocel), transgenic shoots were obtained 3 months and 6 months after incubation, respectively.

The degree of production of RNA in the plant cells can be controlled by suitable choice of promoter sequences, or by selecting the number of copies, or the site of integration, of the DNA sequences according to the invention that are introduced into the plant genome. In this way it may be possible to modify lignification to a greater or lesser extent.

The constructs of our invention may be used to transform cells of both monocotyledonous and dicotyledonous plants in various ways known to the art. In many cases such plant cells (particularly when they are cells of dicotyledonous plants) may be cultured to regenerate whole plants which subsequently reproduce to give successive generations of genetically modified plants. Examples of genetically modified plants according to the present invention include, alfalfa, oil seed rape, sunflower, sorghum, maize, festuca, and trees such as eucalyptus, poplar, and pine.

In the present invention, we use antisense RNA in order to determine the phenotype of transgenic plants which show modified, that is increased or reduced, expression of pPLC4 or pTOMT1 by the use of antisense and sense expression vectors.

BRIEF DESCRIPTION OF THE DRAWINGS

The invention will now be described further with reference to the accompanying drawings, in which:

FIG. 1 shows the complete nucleotide sequence (SEQ ID NO: 1) and deduced amino acid sequence (SEQ ID NO: 2) from pPLC4.

FIG. 2 shows the combined nucleotide sequence (SEQ ID NO: 3) and deduced amino acid sequence of pTOMT1.A and pTOMT1.B.

FIG. 3 shows the nucleotide sequence (SEQ ID NO: 4) of a complete cDNA clone of OMTI from a stem tobacco library.

FIG. 4 is the nucleotide sequence (SEQ ID NO: 6) of a OMT III cDNA isolated from a λZapII library of tobacco leaf.

FIG. 5 shows the construction of antisense and sense vectors using the 5' end 500 bp and the 3' end 900 bp BamH1 fragments from pPLC4.

FIG. 6 shows the construction of an antisense vector using a 1.4 kb PCR fragment containing the complete pPLC4 clone.

DETAILED DESCRIPTION OF THE INVENTION

The invention will now be described by way of illustration in the following Examples.

EXAMPLE 1

Purification of poplar OMTs

A. Isolation procedure

Table 1 shows the ONT activity using caffeic acid as a substrate in young leaves and xylem tissue from poplar trees (*Populus trichocarpa* x *P. deltoides*).

TABLE 1

OMT Activity in young leaves and xylem tissue from poplar trees

| Tissue | Activity/g tissue n kat/g | Specific Activity n kat/g protein |
| --- | --- | --- |
| Leaves | 0.015 | 0.002 |
| Xylem | 0.6 | 0.2 |

There is approximately 50-fold more caffeic acid O-methyltransferase activity in xylem as compared to leaves. Subsequently, OMT activity was purified both from leaves and xylem tissue. The procedure for the purification of the OMTs was established by Dumas et al., (1988). The purification of OMT activity from a total protein extract of poplar leaves via ammonium sulphate precipitation, desalting on Sephadex G25, Q-Sepharose chromatography, and adenosine agarose affinity chromatography, and finally, MonoQ chromatography resulted in one 38-kDa protein. About 5 µg of OMT was obtained from 100 g of leaves. Using xylem as source, several purification steps were omitted. Crude protein extract from 5 g of xylem was applied immediately on an agarose adenosine column leading to the purification of about 50 µg of the 38-kDa OMT with a yield of 50%. At this stage a minor contaminating band of 37-kDa is still visible.

B. Immunological characterisation of poplar OMTs.

Antibodies raised against OMT I and OMT II from tobacco were used to test for cross-reactions with the poplar OMTS. Antibodies raised against OMT II cross-react with the proteins (Mr 38 kDa and 70 kDa) on protein gel blots of proteins purified from leaves by three purification steps (G25, Q-Sepharose, and adenosine agarose affinity chromatography). Antibodies raised against OMT I show weak cross-reaction with a 37-kDa protein. A fourth purification step (chromatography on MonoQ column) resulted in one 38-kDa protein that cross-reacts solely with antibodies directed against OMT II on protein gel blots.

C. Inhibition in vitro of the poplar OMT caffeic acid O-methyltranferase activity by antibodies against OMT II and OMT I from tobacco.

Although the poplar OMT and the tobacco OMT II have a different substrate specificity, the protein gel blots clearly indicate that both enzymes must have similar epitopes recognised by the rabbit antiserum against tobacco OMT II.

Five ng of purified poplar OMTI was mixed with corresponding amounts of antibodies directed against tobacco OMTI and OMTII. After incubation at 37° C., OMT activity towards caffeic acid was measured. The results are given in Table 2 which shows that the caffeic acid OMT activity of the purified poplar OMT can be inhibited by adding antibodies directed against OMT II from tobacco prior to the OMT activity assay (see Materials and Methods). Two and four µl of undiluted rabbit antiserum against tobacco OMT II mixed with purified poplar OMT resulted in a 87% and 92% inhibition, respectively, of the OMT activity. However, 2 µl of undiluted anti-OMT I rabbit antiserum mixed with purified poplar OMT led to a 29% inhibition of the OMT activity. No inhibition of the OMT activity was observed by mixing 2 µl of pre-immune serum with the purified poplar OMT prior to the OMT activity assay.

TABLE 2

Inhibition in vitro of the poplar OMT activity by antibodies directed against OMTI and OMTII from tobacco

| Antibody | OMT activity toward Caffeic acid (%) | Inhibition (%) |
| --- | --- | --- |
| — | 100 | 0 |
| 2 µl anti-OMTI | 71 | 29 |
| 2 µl anti-OMTII | 13 | 87 |
| 4 µl anti OMTII | 8 | 92 |
| 2 µl pre-immune serum | 100 | 0 |

D. Specific activity of the purified poplar OMT towards different phenolic compounds.

The specific activity of the purified OMT towards three different O-diphenolic substrates was measured. Using catechol, caffeic acid, and hydroxyferulic acid as substrate, we found an OMT activity of 0, 30, and 15 nkat/mg protein, respectively.

Previously, it has been shown that OMT 1 from tobacco uses mainly caffeic acid and hydroxyferulic acid as a substrate (Collendavelloo et al., 1981). Therefore, the purified poplar OMT has an OMT I-like enzymatic activity.

EXAMPLE 2

Microsequencing of the 38-kDa OMT.

The 38-kDa protein isolated from poplar xylem tissue was digested with trypsin and the peptides were separated on reverse-phase HPLC. Four peptides were sequenced:

peptide 45 (R/KDLPHVIEDAPSYGVEHVGGDMF)

peptide 49 (LVDVGGGTGAVV)

peptide 51 (GINFDLPHVIEDAP)

peptide 52 (VILVE?ILPVAPD).

Note that peptide 45 is a mixture of two peptides with arginine and lysine, respectively, as first amino acid. Trypsin cleaves proteins after a lysine or arginine residue, except when this is followed by proline, glutamic acid, or aspartic acid. This implies that the first amino acid preceding the sequence of peptide 45 has to be either an arginine or a lysine. The sequences of peptide 45 and 51 are overlapping.

EXAMPLE 3

Design of oligos and cloning of OMT sequences.

Two amino acid sequences of peptide 49 (VDVGGGTGA) and peptide 51 (PHVIEDAP) were chosen to design degenerated oligonucleotides which were subsequently used as primers for a PCR with DNA prepared from a leaf cDNA library of poplar. Since the relative position of the peptide in the protein are unknown, both sense and antisense oligonucleotides were designed. Following the PCR, a 108-bp fragment was found to be amplified with sense primer 49 and antisense primer 51. Using both total RNA from xylem and genomic DNA of poplar, as a template, the same fragment was amplified. The PCR product was subcloned as a blunt-end fragment in the SmaI site of pGem2 yielding plasmid pPLC1. The nucleotide and deduced amino acid sequences are shown in FIG. 1 (positions 661–768).

To isolate a full-length cDNA, the 108-bp fragment was used as a probe to screen a leaf cDNA library from poplar. Three different clones, designated pPLC2, pPLC3, and pPLC4 were identified out of 80,000 clones. The nucleotide sequence of pPLC4 (SEQ ID NO: 1) and the deduced amino acid sequence (SEQ ID NO: 2) are shown in FIG. 1. The cDNA insert is 1375 nucleotides in length and contains one open reading-frame of 1092 nucleotides encoding a protein of 364 amino acids (calculated M 39,720; Pi 5.45). The pPCL2 clone contains a cDNA of 1,420 nucleotides and contains also one ORF of 1,092 nucleotides encoding a protein of 364 amino acids. There is only a 3-amino acid difference between the proteins of the pPCL4 and the pPCL2 clones. Amino acids 97, 191, and 361 in the protein of pPCL2 are leucine, isoleucine, and phenylalanine, respectively. Thus a mixture of at least three closely related isoforms, as shown by the two isoforms present in peptide 45 and by the amino acid sequence of peptide 51 which is entirely found back in the deduced OMT sequence.

EXAMPLE 4

Analysis of the transgenic poplar trees for a modified lignin content

A. Transformation of poplar

With the poplar OMT cDNA clone (pPCL4) five different sense and antisense constructs were made resulting in five plasmids: p35SSOM3A (a 500 bp 5'end fragment in sense), p35SASOM3A (a 500 bp 5' end fragment in antisense), p35SSOM3B (a 900 pb 3' end fragment in sense), p35SASOM3B (a 900 pb 3' end fragment in antisense) and p35SASOM3C (the full length OMT clone in antisense). All the constructs are under the control of the constitutive 35S Cauliflower Mosaic Virus (CaMV) promoter. These constructs were introduced in poplar via an 'Agrobacterium tumefaciens'—mediated transformation of stem explants.

For the plasmids p35SSOM3A (SA), p35SASOM3A (ASA), p35SSOM3B (SB) and p35SASOM3B (ASB) 16,21,7 and 13 independent transformants were regenerated, respectively. Control transformations were performed using plasmid pGSJ780A (this plasmid contains only the 35S CaMV promoter).

2. Estimation of the OMT antisense RNA amount in leaves from ASA and ASB plants.

Using single stranded (ribo) probes (which only hybridise with the antisense RNA) RNA gel blots were performed. The antisense B RNA was detected (strongly) in candidate ASB 5B and candidates ASB 3Am ASB 5A and ASB 7A.

The antisense A RNA levels were high in candidates ASA 1A and candidates ASA 5B, ASA 17A, ASA 6A and ASA 2B. No antisense RNA was detected in transgenic plants containing the pGSJ780A T-DNA. The difference in the antisense RNA levels can be explained by position effects.

3. Steady-state OMT sense RNA in leaves from SA and SB plants.

In an analogous way, by performing Northern blots with single stranded riboprobes which only detect sense RNA, SA and SB plants were analysed.

The sense B RNA can be detected easily in candidates SB 5A and SB 8A and not in candidates SB 2B, SB 4A, SB 7A and SB 10A.

The sense A RNA amount is high in candidates SA 11A and SA 12A, low in candidates SA 9A, SA 18A and SA 23A.

In all the transformants the endogenous OMT mRNA could not be detected (this is in agreement with the fact that the OMT is strongly expressed in xylem and very weak in leaves). All these different transgenics have the same phenotype as the wild type poplar and control plants.

4. OMT activity towards caffeic acid in the transgenic plants.

The OMT activity was measured in different organelles/tissues (Tables 3 and 4). Two candidates (p35SASOM3B 4A and 6A) with a lower OMT activity in petioles, xylem and phloem (two to three times lower) in comparison to wild type and control plants, were identified.

For both these candidates, there was no correlation between the reduced OMT activity and the amount of antisense RNA present in these plants.

5. Lignin analysis of the transgenic poplars.

The transgenic plants were analysed for their lignin composition (Table 5). Lignin is a complex polymer of three different units: p-hydroxyphenyl (H), guaiacyl (G) and syringyl (S) monomers. Poplar lignin contains both guaiacyl and syringyl units. A typical syringyl/guaiacyl (S/G) ratio for poplar is 2/1. Due to the antisense inhibition we expect that the monomer ratio will be modified, resulting in a lower S/G ratio. Lignin characterisation of xylem was performed by the analysis of degradation products recovered from thioacidolysis. This method allows the estimation of the different units, involved in the lignin characteristic structure.

For the wild type and control plants a typical S/G ratio was found (2/1, Table 5). However, the two candidates ASB 4A and ASB 6A have a lower S/G ratio, 1.47 and 1.43, respectively. Like the bm3 maize mutants (these mutants have a lower S/G ratio (0.039) in comparison with wild type maize (1.72) we notice that the S/G ratio of the two ASB poplars has been modified (although not as drastically as was the case for the maize mutants).

TABLE 3

OMT activity in petioles of the different ASB, ASA, SB and SA plants (in cpm).

| Sample | | Replicates | | | Mean |
|---|---|---|---|---|---|
| | | 1 | 2 | 3 | |
| ASB | 6A | — | 2460 | 1252 | 1856 |
| | 8A | 6074 | 5710 | 6931 | 6238 |
| | 4A | 1097 | 1946 | 711 | 1251 |
| | 5B | 2419 | 6295 | 5764 | 4826 |
| ASA | 23A | 1954 | 4342 | 3834 | 3376 |
| | 17A | 5001 | 7596 | 5386 | 5994 |
| | 2B | 2602 | 3926 | 5796 | 4108 |
| SB | 4A | 2527 | 5799 | 5226 | 4517 |
| | 10A | 2252 | 4970 | 5631 | 4284 |
| | 5A | 4726 | 4672 | 4838 | 4755 |
| | 7A | 2686 | 6302 | 7490 | 5492 |
| SA | 13A | 3638 | 5423 | 3697 | 4252 |
| | 3B | 3269 | 4201 | 6875 | 4781 |
| | 2B | 2479 | 6626 | 5842 | 4982 |
| | 7A | 5338 | 8244 | 8691 | 7424 |
| WT | T1 | 3231 | 2843 | 7577 | 4550 |
| | T2 | 3996 | 6171 | 6433 | 5533 |
| | T3 | 3470 | 5152 | 10028 | 6216 |

TABLE 4

OMT activity in xylem and phloem of the candidates
ASB 4A and ASB 6A (in cpm). Mean value, last lane.

|   |   |   | Replicates | |   |
|---|---|---|---|---|---|
| Sample |   | 1 | 2 | 3 | Mean |
| ASB | 4AX | 2465 | 1624 | 743 | 1610 |
|   | F | 3530 | 1108 | 1482 | 2040 |
| ASB | 6AX | 3089 | 1845 | 1152 | 2028 |
|   | F | 4258 | 2063 | 3143 | 3154 |
| WT | T1X | 5040 | 4440 | 2262 | 3914 |
|   | F | 8665 | 5505 | 8809 | 7659 |

WT = Control Plants

TABLE 5

Syringyl/guaiacyl ratio of the different ASB, ASA,
SB and SA plants.

|   |   | Replicates | |   |
|---|---|---|---|---|
| Sample |   | 1 | 2 | Mean |
| ASB | 18A | 2.17 | 2.41 | 2.29 |
|   | 5A | 1.61 | 1.84 | 1.73 |
|   | 4A | 1.34 | 1.60 | 1.47 |
|   | 6A | 1.28 | 1.59 | 1.43 |
| ASA | 7B | 1.93 | 2.48 | 2.20 |
|   | 15A | 1.80 | 2.35 | 2.07 |
|   | 23A | 1.88 | 2.13 | 2.00 |
| SB | 4A | 1.95 | 2.09 | 2.02 |
| SA | 1B | 2.07 | 2.20 | 2.14 |
| WT | T1 | 2.02 | 1.98 | 2.00 |

WT = Control Plants

EXAMPLE 5

Isolation of a tobacco OMT1 clones pTOMT1A and PTOMT1B.

Using similar procedures described for the isolation of the poplar OMT CDNA, a tobacco OMT1 CDNA clones were isolated from a leaf cDNA library prepared from RNA of TMV infected tobacco leaves. These clones were isolated by PCR using sequence information of the purified tobacco OMT1 protein. The combined sequence of two clones covering the complete coding sequence of tobacco OMT1 are shown in FIG. 2 (SEQ ID NO: 3). The underlined part represent sequences found in clone A. the dotted part represents sequences found in clone B.

A complete cDNA clone of OMTI has been isolated from a stem cDNA tobacco library. Its sequence is shown in FIG. 3 (SEQ ID NO:4 and SEQ ID NO: 5).

EXAMPLE 6

Immunoscreening of a λgt11 expression library and characterisation of the MOT III cDNA clone o3.614

The λgt11 phages were plated on *Escherichia coli* Y1090 and fusion proteins induced with 10 mM IPTG. The proteins bound to nitro-cellulose filters were screened by immunodetection using anti-tobacco OMT III polyclonal antibody (Hermann et al., 1987; Dumas, 1990). Three positive clones were purified after immunoscreening of the λgt11 library. The length of their CDNA inserts was determined by PCR. Aliquots of phage lysates (5μl) were heated for 5 mins at 94° C. and used as template for PCR. The amplification mixture consists of 10 mM Tri-HCl pH 8.3, 11 mM KCl, 1.6mM MgCl$_2$, 1 mM DTT, 200 μM each dNTP, 1 μM each oligonucleotide primer, and 1 unit of Taq polymerase (Beckman) in a final volume of 50 μl. The amplification program consisted of 25 cycles of denaturation (94° C., 1 min), annealing (40° C., 1 min), and primer extension (72° C., 1 min). The longest clone, named o3.614, was 614 bp long and was submitted to phage amplification and DNA purification by CsCl gradient (4). The 614 bp cDNA insert was subloned by EcoRI restriction digestion in pBluescript KS(+)(Stratagene, Inc). According to standard methods (4), deletion from both the extremities of the plasmid were generated by ExoIII-Mung Bean digestions and the primers and the T7 DNA polymerase.

EXAMPLE 7

Construction and screening of a λZapII cDNA library from tobacco leaf RNA and characterisation of a complete clone Poly(A)+RNA from 48 hours TMV infected leaves was used to construct an oligo(dT) primed CDNA. Double-stranded cDNA was ligated to hemi-phosphorylated EcoR I/Not I adaptors (Pharmacia), ligated into λZapII vector (Stratagene, Inc) and packaged using Gigapack in vitro packaging extracts (Stratagene, Inc). The resulting cDNA library titled 1.8×10$^7$ pfu/μg cDNA. The o3.614 clone was used as DNA probe. The 614 bp DNA fragment was purified from purified from 0.8% agarose gel (PrepAGene, BIORAD), 32p labelled by random oligonucleotide-primed synthesis and used to screen a λZapII library made by standard protocols (4). After three cycles of screening, twelve positive clones were isolated from approximately 1.8×10$^5$ plaque-forming units. cDNA inserts from positive phage were rescued as Bluescript plasmids by R408 helper phage mediated in vivo excision, as described by the manufacture (Stratagene, Inc). Cloned insert DNA was isolated by Not I digestion and analysed on 1% agarose gels. The CDNA clones isolated from λZapII CDNA library were mapped with restriction endonucleases and then sequenced on both strands by the dideoxy chain termination method 95) using T7 DNA polymerase (Pharmacia). For sequencing the internal regions, synthetic oligonucleotide primers (18 mers) were designed from the DNA sequence previously determined. The complete sequence of a OMT III cDNA clone is given in FIG. 4 (SEQ ID NO:6 and SEQ ID NO:7). The amino acid sequences of peptides obtained by trypsic digestion of the purified OMT II and OMT III proteins all correspond to the aminoacid sequence derived from OMT III cDNA clones. These evidences suggest the occurrence of only one mRNA species for the "Pathogenesis-Related" forms OMT II and OMT III but of 2 forms for the lignification-related OMT I.

EXAMPLE 8

Localisation of OMT I transcripts by in situ hybridisation.

In petiole sections, OMT I mRNAs were localised in parenchyma cells of xylem and phloem, with a marked signal around the nuclei. In leaf sections, OMT I mRNAs were found to accumulate particularly in the upper and lower epidermis in a ring of tissue surrounding TMV-induced necrotic lesions, were no cell-type specific hybridisation was found in the healthy leaf.

EXAMPLE 9

Design of antisense vectors

Five different poplar OMT antisense constructs have been made. A 500 bp BamHI fragment corresponding to the 5' end of the poplar OMT clone and a 900-bp BamHI fragment corresponding to the 3' end of the poplar OMT clone were cloned in the BamHI site of vector pGSJ780A, in both sense and antisense direction yielding the four plasmids p35SSOM3A, p35SASOM3A, p35SASOM3A, p35SSOM3B, and p35SASOM3B (FIG. 5). All OMT fragments are under the control of the CaMV 35S promoter. The full-length OMT clone was cloned in the vector pGSJ780A in antisense direction by PCR yielding plasmid p35SASOM3C (FIG. 6). The correct direction of the inserts has been confirmed by sequencing. The vector pGSJ780A is a binary vector with the pVS1 origin of replication and a Sm/Sp resistance gene for selection in *Agrobacterium tumefaciens*. Between the T-DNA borders there is a nos-nptII-ocs cassette and a multiple cloning site).

The construction of the tobacco antisense vector follows that described for the poplar vectors. The insert was inserted into the vector pGSJ780A.

We claim:

1. Isolated DNA encoding caffeic acid O-methyl transferase in the clones pTOMT1.A and pTOMT1.B and variants of said DNA encoding the same amino acid sequences.

2. Isolated DNA comprising the DNA claimed in claim 1 under control of a transcriptional control sequence operative in plants.

3. An isolated DNA as claimed in claim 2, for the down-regulation of lignin biosynthesis in which the said DNA is in antisense orientation.

4. An isolated DNA as claimed in claim 2, for the amplification of lignin biosynthesis, in which the said DNA is in sense orientation.

5. Isolated DNA comprising a transcriptional initiation region operative in plants operatively linked to a DNA sequence encoding RNA complementary to an MRNA encoding the protein produced by the gene in pTOMT1A or pTOMT1.B so as to initiate production of MRNA therefrom.

6. Isolated DNA having the nucleotide sequence given in FIG. 2 (SEQ ID NO:3).

7. Isolated DNA having the nucleotide sequence given in FIG. 3 (SEQ ID NO:4).

8. Isolated DNA having the nucleotide sequence given in FIG. 4 (SEQ ID NO:6).

9. A plant cell, and a plant derived therefrom having stably incorporated in its genome by transformation a DNA as claimed in claim 1 in sense or antisense orientation, and the fruit and seeds of said plants.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 1368 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
CACCTTCTTC AACCTTTTGT TTCCTTAAAG AATTCAATCT TGATCAAGAT GGGTTCAACA      60

GGTGAAACTC AGATGACTCC AACTCAGGTA TCAGATGAAG AGGCACACCT CTTTGCCATG     120

CAACTAGCCA GTGCTTCAGT TCTACCAATG ATCCTCAAAA CAGCCATTGA ACTCGACCTT     180

CTTGAAATCA TGGCTAAAGC TGGCCCTGGT GCTTTCTTGT CCACATCTGA GATAGCTTCT     240

CACCTCCCTA CCAAAAACCC TGATGCGCCT GTCATGTTAG ACCGTATCTT GCGCCTCCTG     300

GCTAGCTACT CCATACTGAC TTGCTCTCTG AAAGATCATC CTGATGGGAA AGTTGAGAGA     360

CTGTATGGCC TTGCTCCTGT TTGCAAATTC TTGACCAAGA ACGAGGACGG TGTCTCTGTC     420

AGCCCTCTCT GTCTCATGAA CCAGGACAAG GTCCTCATGG AAAGCTGGTA TTATTTGAAA     480

GATGCAATTC TTGATGGAGG AATTCCATTT AACAAGGCCT ATGGGATGAC TGCATTTGAA     540

TATCATGGCA CGGATCCAAG ATTCAACAAG GTCTTCAATA AGGGAATGTC TGACCACTCT     600

ACCATTACCA TGAAGAAGAT TCTTGAGACC TACAAAGGCT TTGAAGGCCT CACATCCTTG     660

GTGGATGTTG GTGGTGGGAC TGGAGCTGTC GTTAACACCA TCGTCTCTAA ATACCCTTCA     720

ATTAAGGGCA TTAACTTTGA TTTGCCCCAC GTCATTGAGG ATGCCCCATC TTATCCCGGT     780

GTGGAGCATG TTGGTGGGGA CATGTTTGTT AGTGTGCCCA AAGCAGATGC CGTTTTCATG     840

AAGTGGATAT GCCATGATTG GAGCGACGCA CACTGCTTAA AATTCTTGAA GAATTGCTAT     900

GACGCCTTGC CGGAAAACGG CAAGGTGATA CTTGTTGAGT GCATTCTTCC CGTGGCTCCT     960

GACACAAGCC TTGCCACCAA GGGAGTCGTT CACATTGATG TTATCATGCT GGCGCACAAC    1020

CCCGGTGGGA AAGAGAGGAC CGAAAAGGAA TTTGAGGGCT TAGCTAAGGG AGCTGGCTTT    1080

CAAGGTTTTG AAGTGATGTG CTGTGCATTC AACACACATG TCATTGAACT CCGCAAGAAC    1140

TAAGGCTCAA GTCCAAGCTC CAAGTTACTT GGGGTTTTCC ATACAACGTT GCTGCTGTCT    1200

CTGCTTTTGA TGTTGTGATT GCTTTTTTAC ATGACGAGTA GCTTTCTCTT ATGAAACATG    1260

TAAGGTTAAG GTTGCGTTTT GTATGCCTGA TTTTCTCAAA TAACTTCACT GCCTCCCTCA    1320

AAATTCTTAA TACATGTGAA AAGATTTCTT AAAAAAAAAA AAAAAAA                  1368
```

(2) INFORMATION FOR SEQ ID NO:2:

(i) SEQUENCE CHARACTERISTICS:
    (A) LENGTH: 364 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:2:

```
Met Gly Ser Thr Gly Glu Thr Gln Met Thr Pro Thr Gln Val Ser Asp
  1               5                  10                  15

Glu Glu Ala His Leu Phe Ala Met Gln Leu Ala Ser Ala Ser Val Leu
                 20                  25                  30

Pro Met Ile Leu Lys Thr Ala Ile Glu Leu Asp Leu Leu Glu Ile Met
             35                  40                  45

Ala Lys Ala Gly Pro Gly Ala Phe Leu Ser Thr Ser Glu Ile Ala Ser
 50                  55                  60

His Leu Pro Thr Lys Asn Pro Asp Ala Pro Val Met Leu Asp Arg Ile
 65                  70                  75                  80

Leu Arg Leu Leu Ala Ser Tyr Ser Ile Leu Ile Cys Ser Leu Lys Asp
                 85                  90                  95

His Pro Asp Gly Lys Val Glu Arg Leu Tyr Gly Leu Ala Pro Val Cys
            100                 105                 110

Lys Phe Leu Thr Lys Asn Glu Asp Gly Val Ser Val Ser Pro Leu Cys
            115                 120                 125

Leu Met Asn Gln Asp Lys Val Leu Met Glu Ser Trp Tyr Tyr Leu Lys
130                 135                 140

Asp Ala Ile Leu Asp Gly Gly Ile Pro Phe Asn Lys Ala Tyr Gly Met
145                 150                 155                 160

Thr Ala Phe Glu Tyr His Gly Thr Asp Pro Arg Phe Asn Lys Val Phe
                165                 170                 175

Asn Lys Gly Met Ser Asp His Ser Thr Ile Thr Met Lys Lys Ile Leu
            180                 185                 190

Glu Thr Tyr Lys Gly Phe Glu Gly Leu Thr Ser Leu Val Asp Val Gly
            195                 200                 205

Gly Gly Thr Gly Ala Val Val Asn Thr Ile Val Ser Lys Tyr Pro Ser
            210                 215                 220

Ile Lys Gly Ile Asn Phe Asp Leu Pro His Val Ile Glu Asp Ala Pro
225                 230                 235                 240

Ser Tyr Pro Gly Val Glu His Val Gly Gly Asp Met Phe Val Ser Val
                245                 250                 255

Pro Lys Ala Asp Ala Val Phe Met Lys Trp Ile Cys His Asp Trp Ser
            260                 265                 270

Asp Ala His Cys Leu Lys Phe Leu Lys Asn Cys Tyr Asp Ala Leu Pro
            275                 280                 285

Glu Asn Gly Lys Val Ile Leu Val Glu Cys Ile Leu Pro Val Ala Pro
            290                 295                 300

Asp Thr Ser Leu Ala Thr Lys Gly Val Val His Ile Asp Val Ile Met
305                 310                 315                 320

Leu Ala His Asn Pro Gly Gly Lys Glu Arg Thr Glu Lys Glu Phe Glu
                325                 330                 335

Gly Leu Ala Lys Gly Ala Gly Phe Gln Gly Phe Glu Val Met Cys Cys
            340                 345                 350

Ala Phe Asn Thr His Val Ile Glu Leu Arg Lys Asn
            355                 360
```

(2) INFORMATION FOR SEQ ID NO:3:

(i) SEQUENCE CHARACTERISTICS:
        (A) LENGTH: 1244 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GCCGGCCCGG GCGCGGCGAT TTCTCCTTCT GAATTAGCTG CTCAGCTCTC AACCCAGAAC      60
CCAGAAGCAC CCGTTATGCT TGATCGGATG CTTAGGCTAC TTGCTACTTA CTCTGTTCTC     120
AATTGTACTC TTAGAACACT GTCTGATGGC AGTGTTGAGA GGCTTTATAG TCTGGCTCCG     180
GTTTGTAAGT TCTTGACTAA GAATGCTGAT GGTGTTTCTG TTGCCCCACT TTTGCTTATG     240
AATCAAGATA AAGTTCTTAT GGAGAGCTGG TACCACTTAA AAGATGCAGT ACTAGATGGT     300
GGAATCCCAT TCAACAAGGC CTATGGAATG ACAGCATTTG AGTACCATGG CACAGATCCA     360
AGATTCAACA AAGTTTTCAA CCGTGGAATG TCTGATCACT CCACTATGTC AATGAAAAAG     420
ATTCTTGAGG ACTACAAAGG ATTTGAAGGC CTAAATTCCA TTGTCGATGT TGGTGGTGGA     480
ACTGGCGCTA CTGTTAACAT GATTGTCTCC AAACATCCCT CTATTAAGGG TATTAACTTT     540
GATTTACCAC ATGTTATTGG AGATGCTCCA GCTTACCCTG GTGTCGAGCA CGTTGGTGGC     600
GACATGTTTG CCAGTGTGCC AAAAGCAGAT GCCATTTTCA TGAAGTGGAT TTGTCATGAT     660
TGGAGCGACG AGCATTGCCT AAAATTCTTG AAGAATTGCT ATGAAGCACT ACCTGCAAAT     720
GGGAAGGTGA TAATAGCGGA GTGCATACTT CCAGAGGCCC CAGATACATC ACTTGCAACT     780
AAGAATACAG TACATGTTGA TATTGTGATG TTAGCACATA ACCCAGGAGG CAAAGAAAGG     840
ACTGAGAAGG AATTTGAGGC TTTGGCTAAG GGCGCTGGTT TTACTGGATT CGCAAGGCTT     900
GTTGCGCTTA CAACACTTGG GTCATGGAAT TCAACAAATA ATTAATCGAT TCCTTTGGAG     960
AATTAAGCAA TATACTGTTC ATTTTGCATT TTGAAATTCT ACTTTTCACA GAGTGGCTTT    1020
ACTGCGAAAT AAAAGAAATA TATAGCTTTT ACCTTGAAAA GATCAATGTT CAAAGGGAAA    1080
AAAAAAAGGA AGATGAAATA ATTGCTCTCA GAAAAGCAGT GTGTTAGGAA AAAGCTTTTT    1140
AGCTGGATTT TGAATTTTTA TTGTATGTAT TTCTGTAATA CACATGTATT GAAGGAATAC    1200
TAGTTTTCGA CCAATCATAT TTCTTTGAAA AAAAAAAAAA AAAA                    1244
```

(2) INFORMATION FOR SEQ ID NO:4:

(i) SEQUENCE CHARACTERISTICS:
        (A) LENGTH: 1430 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
ATTCCTTCAA CTTACCCAAT TAAGTCATCG AAAAATCTGA AACAGAACTA AAAGTAAAAT      60
GGGTTCAACA AGCGAGAGCC AGAGTAACAG TCTCACTCAC ACAGAAGACG AAGCTTTCTT     120
ATTTGCCATG CAATTGTGTA GTGCTTCTGT ACTTCCTATG GTCCTAAAAT CAGCCGTAGA     180
ACTTGACCTT CTTGAGCTAA TGGCTAAGGC TGGTCCAGGT GCAGCTATTT CTCCTTCTGA     240
ATTAGCTGCT CAGCTCTCAA CTCAGAACCC AGAAGCACCT GTTATGCTTG ATCGGATGCT     300
TAGGCTACTT GCTTCTTACT CTGTTCTCAA TTGTACTCTT AGAACACTGC CTGATAGCAG     360
```

```
TGTTGAGAGG CTTTATAGTC TGGCTCCCGT CTGTAAGTAC TTGACTAAGA ATGCTGATGG      420

TGTTTCTGTT GCCCCACTTT TGCTTATGAA TCAAGATAAA GTTCTTATGG AGAGCTGGTA      480

CCACTTAAAA GATGCAGTAC TAGATGGCGG AATCCCATTC AACAAAGCCT ATGGAATGCA      540

AGCATTTGAG TACCATGGCA CAGATCCAAG ATTCAACAAA GTGTTCAACC GTGGAATGTC      600

TGATCACTCC ACTATGTCAA TGAAGAAGAT TCTTGAGGAC TACAAAGGAT TTGAAGGCCT      660

AAATTCCATT GTTGATGTTG GTGGTGGAAC GGGTGCTACT GTTAACATGA TTGTCTCTAA      720

ATATCCCTCT ATTAAGGGCA TTAACTTTGA TTTGCCACAT GTAATTGGAG ATGCTCCAAC      780

TTACCCCGGT GTCGAGCACG TTGGTGGCGA CATGTTTGCT AGTGTGCCAA AGCAGATGCC      840

ATTTTCATGA AGTGGATTTG TCATGATTGG AGCGATGAGC ATTGCCTAAA ATTCTTGAAG      900

AATTGCTATG AAGCACTACC TGCAAATGGG AAGGTGATAA TTGCAGAGTG CATACTTCCA      960

GAGGCCCCAG ATACATCACT TGCAACTAAG AATACAGTAC ATGTTGATAT TGTTATGTTA     1020

GCACATAACC CAGGAGGCAA AGAAAGGACT GAGAAGGAAT TTGAGGCTTT GGCTAAGGGC     1080

GCTGGTTTTA CTGGATTCGC AAGGCTTGTT GCGCTTACAA CACTTGGGTC ATGGAATTCA     1140

ACAAGTAATT AATCGATTCC TTAATTTGAA GGATTAAGCA ATATACTGTT CGTTTTGCAT     1200

TTGGAAATTC TACTTTTCTC AGAGTGGCTT GACTGTGAAA TAAAAGAAAT ATAGCTTTTA     1260

ACTTGAAAAG ATTGATGTTC AAAAGAAAAA AGGAAGATG AAATAATTGC TCTCAGAAAA     1320

GCAATGTGTT AGGAAAAAGC TTTTTTAGCT GGATTTTGAA TTTTACTGTA TGTATTTCTG     1380

TTATACACAT GTATTGAAGG AATACTAGTT TTCGACCAAA AAAAAAAAA                 1430
```

(2) INFORMATION FOR SEQ ID NO:5:

(i) SEQUENCE CHARACTERISTICS:
        (A) LENGTH: 364 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Gly Ser Thr Ser Glu Ser Gln Ser Asn Ser Leu Thr His Thr Glu
1               5                   10                  15

Asp Glu Ala Phe Leu Phe Ala Met Gln Leu Cys Ser Ala Ser Val Leu
            20                  25                  30

Pro Met Val Leu Lys Ser Ala Val Glu Leu Asp Leu Leu Glu Leu Met
        35                  40                  45

Ala Lys Ala Gly Pro Gly Ala Ala Ile Ser Pro Ser Glu Leu Ala Ala
    50                  55                  60

Gln Leu Ser Thr Gln Asn Pro Glu Ala Pro Val Met Leu Asp Arg Met
65                  70                  75                  80

Leu Arg Leu Leu Ala Ser Tyr Ser Val Leu Asn Cys Thr Leu Arg Thr
                85                  90                  95

Leu Pro Asp Ser Ser Val Glu Arg Leu Tyr Ser Leu Ala Pro Val Cys
            100                 105                 110

Lys Tyr Leu Thr Lys Asn Ala Asp Gly Val Ser Val Ala Pro Leu Leu
        115                 120                 125

Leu Met Asn Gln Asp Lys Val Leu Met Glu Ser Trp Tyr His Leu Lys
    130                 135                 140

Asp Ala Val Leu Asp Gly Gly Ile Pro Phe Asn Lys Ala Tyr Gly Met
145                 150                 155                 160

Thr Ala Phe Glu Tyr His Gly Thr Asp Pro Arg Phe Asn Lys Val Phe
```

|     | 165 | 170 | 175 |     |
|-----|-----|-----|-----|-----|

Asn Arg Gly Met Ser Asp His Ser Thr Met Ser Met Lys Lys Ile Leu
            180                 185                 190

Glu Asp Tyr Lys Gly Phe Glu Gly Leu Asn Ser Ile Val Asp Val Gly
            195                 200                 205

Gly Gly Thr Gly Ala Thr Val Asn Met Ile Val Ser Lys Tyr Pro Ser
            210                 215                 220

Ile Lys Gly Ile Asn Phe Asp Leu Pro His Val Ile Gly Asp Ala Pro
225                 230                 235                 240

Thr Tyr Pro Gly Val Glu His Val Gly Gly Asp Met Phe Ala Ser Val
            245                 250                 255

Pro Lys Ala Asp Ala Ile Phe Met Lys Trp Ile Cys His Asp Trp Ser
            260                 265                 270

Asp Glu His Cys Leu Lys Phe Leu Lys Asn Cys Tyr Glu Ala Leu Pro
            275                 280                 285

Ala Asn Gly Lys Val Ile Ile Ala Glu Cys Ile Leu Pro Glu Ala Pro
            290                 295                 300

Asp Thr Ser Leu Ala Thr Lys Asn Thr Val His Val Asp Ile Val Met
305                 310                 315                 320

Leu Ala His Asn Pro Gly Gly Lys Glu Arg Thr Glu Lys Glu Phe Glu
            325                 330                 335

Ala Leu Ala Lys Gly Ala Gly Phe Thr Gly Phe Ala Arg Leu Val Ala
            340                 345                 350

Leu Thr Thr Leu Gly Ser Trp Asn Ser Thr Ser Asn
            355                 360

(2) INFORMATION FOR SEQ ID NO:6:

(i) SEQUENCE CHARACTERISTICS:
        (A) LENGTH: 1471 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
AACAAAAACA CTCTAAAAGG AAAAGACTAG GAGAATAATT ACACTACAAC TCTTATAGCT    60

AATTCTTGTC TCAAGATTTT CACCTATGGA ATCCTCAACC AAAAGCCAAA TACCAACACA   120

ATCAGAAGAA GAGCGTAACT GCACATATGC CATGCAACTA TTGTCATCTT CAGTCCTCCC   180

CTTTGTGTTG CATTCAACAA TTCAATTGGA AGTTTTTGAG ATATTAGCCA AATCTAATGA   240

CACTAAACTT TCTGCTTCTC AAATTGTTTC TCAAATTCCT AACTGCAAGA ATCCTGATGC   300

AGCTACTATG TTAGATAGGA TGCTTTATGT GTTGGCTAGT TACTCGTTGT TTACTTGTTC   360

CATTGTTGAG GATGAAGAAA ATAATGGGGG CCAGAAAAGA GTGTATGGTT TGTCACAAGT   420

GGGAAAATTC TTTGTTAGAG ATGAAGATGG TGCATCAATG GGGCCACTTT TGGCTTTGCT   480

TCAAGATAAA GTATTCATAA ACAGCTGGTT TGAACTAAAA GATGCAGTTC TTGAAGGAGG   540

AGTTCCATTT GACAGGGTAC ACGGTGTTGT CCATGCATTT GAATATCCAA AATCGGACCC   600

AAAATTCAAT GATGTTTTCA ACAAGGCAAT GATCAATCAC ACAACTGTAG TCATGAAAAA   660

AATACTTGAA AATTACAAAG GTTTTGAGAA CCTTAAAACT TTGGTTGATG TTGGAGGTGG   720

TCTTGGAGTT AACCTCAAGA TGATTACATC TAAATACCCC ACAATTAAGG GCACTAATTT   780

TGATTTGCCA CATGTTGTTC AACATGCCCC TTCCTATCCT GGGGTGGAAC ATGTTGGGGG   840

AGATATGTTT GAAAGTGTTC CAGAAGGAGA TGCTATTTTT ATGAAGTGGA TTCTTCATGA   900
```

-continued

```
CTGGAGTGAT AGTCACAACC TCAAGTTGCT AAAGAACTGC TACAAGGCTC TACCAGACAA    960

TGGAAAGGTG ATTGTTGTTG AGGCCATTTT ACCAGTGAAA CCAGACATTG ACACCGCAGT   1020

GGTTGGCGTT TCGCAATGTG ATTTGATCAT GATGGCTCAA AATCCTGGAG GCAAAGAGCG   1080

ATCGGAAGAG GAGTTTCGAG CCTTGGCTAC TGAAGCTGGA TTCAAAGGCG TTAACTTAAT   1140

ATGTTGTGTC TGTAATTTTT GGGTCATGGA ATTCTGCAAG TAGATTTCTA CTGTACATTG   1200

AGTTTCTACT ACTCTTGAGT ATCCATTTAT GGCAATCTGG GACTGGAATT GCAGCTTAGT   1260

CCAGATTGAA CATTGATATT CCTAATAATA TTTCTATTAT TTCCCTTGTT TATTTCTCTT   1320

GTATGAAAGG ATGTCATTTT GAGTATTGAT AATCATGTTC TCTAGGACAG AAATTGTAAC   1380

TTTGTCCAAC TTTATTGATA TTCCTAGTAA GATTTATATG ACATGTGTCT CTGGTTTGAG   1440

AAGAGTTTCA ATATCTAAAA AAAAAAAAA A                                   1471
```

(2) INFORMATION FOR SEQ ID NO:7:

(i) SEQUENCE CHARACTERISTICS:
        (A) LENGTH: 365 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Glu Ser Ser Thr Lys Ser Gln Ile Pro Thr Gln Ser Glu Glu
1               5                   10                  15

Arg Asn Cys Thr Tyr Ala Met Gln Leu Leu Ser Ser Val Leu Pro
                20                  25                  30

Phe Val Leu His Ser Thr Ile Gln Leu Glu Val Phe Glu Ile Leu Ala
            35                  40                  45

Lys Ser Asn Asp Thr Lys Leu Ser Ala Ser Gln Ile Val Ser Gln Ile
        50                  55                  60

Pro Asn Cys Lys Asn Pro Asp Ala Ala Thr Met Leu Asp Arg Met Leu
65                  70                  75                  80

Tyr Val Leu Ala Ser Tyr Ser Leu Phe Thr Cys Ser Ile Val Glu Asp
                85                  90                  95

Glu Glu Asn Asn Gly Gly Gln Lys Arg Val Tyr Gly Leu Ser Gln Val
                100                 105                 110

Gly Lys Phe Phe Val Arg Asp Glu Asp Gly Ala Ser Met Gly Pro Leu
            115                 120                 125

Leu Ala Leu Leu Gln Asp Lys Val Phe Ile Asn Ser Trp Phe Glu Leu
        130                 135                 140

Lys Asp Ala Val Leu Glu Gly Gly Val Pro Phe Asp Arg Val His Gly
145                 150                 155                 160

Val Val His Ala Phe Glu Tyr Pro Lys Ser Asp Pro Lys Phe Asn Asp
                165                 170                 175

Val Phe Asn Lys Ala Met Ile Asn His Thr Thr Val Val Met Lys Lys
            180                 185                 190

Ile Leu Glu Asn Tyr Lys Gly Phe Glu Asn Leu Lys Thr Leu Val Asp
        195                 200                 205

Val Gly Gly Gly Leu Gly Val Asn Leu Lys Met Ile Thr Ser Lys Tyr
210                 215                 220

Pro Thr Ile Lys Gly Thr Asn Phe Asp Leu Pro His Val Val Gln His
225                 230                 235                 240

Ala Pro Ser Tyr Pro Gly Val Glu His Val Gly Gly Asp Met Pro Phe
```

```
                        245                 250                 255
Ser Val Pro Glu Gly Asp Ala Ile Phe Met Lys Trp Ile Leu His Asp
            260                 265                 270

Trp Ser Asp Ser His Asn Leu Lys Leu Leu Lys Asn Cys Tyr Lys Ala
        275                 280                 285

Leu Pro Asp Asn Gly Lys Val Ile Val Val Glu Ala Ile Leu Pro Val
        290                 295                 300

Lys Pro Asp Ile Asp Thr Ala Val Val Gly Val Ser Gln Cys Asp Leu
305                 310                 315                 320

Ile Met Met Ala Gln Asn Pro Gly Gly Lys Glu Arg Ser Glu Glu Glu
                325                 330                 335

Phe Arg Ala Leu Ala Thr Glu Ala Gly Phe Lys Gly Val Asn Leu Ile
            340                 345                 350

Cys Cys Val Cys Phe Pro Trp Val Met Glu Phe Cys Lys
            355                 360                 365
```